United States Patent [19]
Lee

[11] Patent Number: 4,506,019
[45] Date of Patent: Mar. 19, 1985

[54] ACTIVATED POLYMER CONTAINER MEANS AND ASSAY METHOD EMPLOYING THE SAME

[75] Inventor: Jin P. Lee, Troy, Mich.

[73] Assignee: Leeco Diagnostics, Inc., Southfield, Mich.

[21] Appl. No.: 422,801

[22] Filed: Sep. 24, 1982

[51] Int. Cl.³ .................. G01N 33/54; B65D 71/00; G01N 23/06
[52] U.S. Cl. .................. 436/500; 422/68; 422/69; 422/71; 436/531; 436/810; 436/823
[58] Field of Search .............. 436/500, 531, 810, 823; 422/68, 69, 71

[56] References Cited

U.S. PATENT DOCUMENTS

| | | | |
|---|---|---|---|
| 3,938,953 | 2/1976 | Paschalis et al. | 436/500 |
| 3,969,287 | 7/1976 | Jaworek et al. | 260/112 R |
| 4,081,402 | 3/1978 | Levy et al. | 436/500 |
| 4,147,764 | 4/1979 | Levy et al. | 436/500 |
| 4,166,102 | 8/1979 | Johnson | 436/804 |
| 4,255,412 | 3/1981 | Albert | 436/500 |

OTHER PUBLICATIONS

Sundaram, Biochem. J., 183(1979), 445–451.
Morris et al., Biochem. J., 147(1975), 593–603.

Primary Examiner—Christine M. Nucker
Attorney, Agent, or Firm—Krass and Young

[57] ABSTRACT

Novel activated polyamide polymer container or test tube means and a method for the determination of ligand or analyte content in aqueous samples, are provided. The surfaces of the container tubes are specially activated thermally during their manufacture by injection molding thereby avoiding the need for subsequent coating of the tubes, e.g., with antibody, for binding assay procedures.

20 Claims, No Drawings

ACTIVATED POLYMER CONTAINER MEANS AND ASSAY METHOD EMPLOYING THE SAME

DESCRIPTION

The present invention relates to a novel method and means for the determination of ligand or analyte content in aqueous samples, especially biological or clinical samples, e.g., body fluids such as blood serum. According to the method, the substance to be determined is bound to the surface of a unique thermally activated polymer container tube or test tube containing the aqueous sample so that, in tracer or labeled form, the ligand can be readily measured by decanting the residual liquid sample from the container and reading or counting either the unique solid phase container or the separate liquid phase or both.

BACKGROUND OF THE INVENTION

Various diagnostic assays for in vitro determination of ligands in body fluid are known, including specifically: radioimmunoassay (RIA), competitive protein-binding radioassay (CPB), enzyme immunoassay (EIA), enzyme multiplied immunological technique (EMIT), enzyme linked immunosorbent assay (ELISA), fluorescent immunoassay (FIA), and hemagglutination inhibition (HAI) assay. The assays are based on the principle of optimizing the mutual affinity between the ligand and a specific antibody or other binding entity for that ligand. For a comprehensive review of methods and methodology, see Weetal's Immobilized Enzymes, Antigens, Antibodies, and Peptides, Chapters 4 and 9, Marcel DEKKER, Inc., New York, 1975, incorporated herewith by reference.

In one prior art procedure, described in U.S. Pat. No. 3,464,798, a surface active plastic stick inserted in a conventional test tube is used for binding an analyte for clinical assay purposes. A disadvantage of this procedure is that such a plastic stick must be specially fabricated, is costly to produce, and is inconvenient to work with.

In another prior art procedure, described in U.S. Pat. No. 3,646,346, the determination of proteins in aqueous samples is done by an RIA procedure in which for binding purposes the interior surface of plastic tubes is first coated with specific antibody and the resulting coated tubes are used for containing the samples and binding the labeled and unlabeled antibody-specific protein in the samples to provide an end point distribution that is readable as a quantitative showing of specific protein content of each sample. A difficulty with this procedure is that the coated tubes have to be specially prepared commercially or in house, and, must thereafter be maintained under refrigeration prior to use.

It is therefore an object of the present invention to provide polymer container means and an assay method employing the same which avoids the disadvantages of the prior art practices.

It is a further object of the invention to provide novel container means and an assay method employing the same which avoid the use of coated assay tubes and disadvantages thereof.

It is a still further object to provide novel container means for assay purposes that are cost-effective and readily adaptable to a wide variety of applications in analytical and clinical chemistry.

These and other objects, features and advantages of the present invention will become apparent from the following description of the invention and preferred embodiments thereof.

SUMMARY AND DETAILED DESCRIPTION

In one aspect, the invention concerns a novel assay method for the determination of ligand content in aqueous samples. The method comprises the steps of providing a plurality of molded polyamide polymer test tubes each having a ligand-free inner wall surface of given area formed with thermally activated ligand-specific binding sites such that the ligand binding capacity for assay purposes is uniform from tube to tube, further providing a tube set comprising said tubes each containing an aqueous sample of unlabeled ligand in admixture with labeled ligand and ligand binding protein, and further ones of said tubes containing comparable standards and controls, incubating the mixtures contained in the tubes to achieve an end point wherein labeled and unlabeled ligand is bound to the respective tubes as a solid phase while unbound labeled and unlabeled ligand remains in the respective tubes as a liquid phase, separating the respective solid and liquid phases for each sample, and measuring the ligand content with respect to each sample as a function of the label value of at least one of the phases for that sample in relation to the standards and controls. The method is unique, and importantly so, in that it obviates the need for plastic stick inserts or for pre-coating test tubes with antibody to achieve the desired binding. Thus, it is no longer necessary to specially coat tubes or to refrigerate coated tubes as in the prior art. As described in what follows, the test tubes according to the invention can be kept indefinitely, at ambient temperature, for long periods without special precautions.

As indicated, the method is applicable to a wide variety of aqueous samples, especially biological or clinical samples, that are of interest for in vitro research, laboratory, quality control, product development, monitoring, and survey use. The method is useful for the selective separation of a dissolved substance from test mixtures, such as antigen, hapten, antibody, carrier protein, enzyme, ligand, analyte, compound inhibitor, and other such substance, hereinafter referred to for simplicity as a ligand. For example, the method of the invention contemplates use for the assay of the following ligands:

| Peptide Hormones | |
| --- | --- |
| Growth hormone (GH) | Human chorionic gonadotropin (HCG) |
| Luteinizing hormone (LH) | Insulin |
| Follicle-stimulating hormone (FSH) | Secretin |
| Thyroid-stimulating hormone (TSH) | Gastrin |
| Adrenocorticotropic hormone (ACTH) | α-Melanocyte-stimulating hormone |
| Prolactin | β-Melanocyte-stimulating hormone |
| Oxytocin | Parathyroid hormone |
| Vasopressin | Calcitonin |
| TSH-releasing factor | Angiotensin |
| LH-releasing factor | Proinsulin |
| | Bradykinin |
| Steroids | |
| Estrogens | Cortisol |
| Testosterone | Aldosterone |
| Androstenedione | 11-Deoxycortisol |
| Progesterone | Deoxycorticosterone |
| Drugs | |
| Digoxin | Morphine |
| Digitoxin | Barbiturates |

-continued

| Lysergic acid diethylamide | Ouabain | |
| --- | --- | --- |
| Miscellaneous | | |
| Prostaglandins | Folic acid | Vitamin $B_{12}$ |
| Cyclic AMP | Cyclic GMP | Triiodothyronine |
| Thyroxine | IgE | Plasminogen |
| Hepatitis-associated antigen | Carcinoembryonic Antigen | Messenger RNA |

Small, reactive molecules such as amino acids will bond directly to the reactive surface of the test tubes of the present invention. Larger molecules, such as enzymes, polypeptide hormones, antibodies and other proteins, as is contemplated, will bond to the reactive surface by use of coupling agents, such as glutaraldehyde and carbodiimides. Spacer molecules, for example, L-lysine, may be interposed during the coupling to minimize effects of steric hindrance during assay. For coupling, etc., one may use techniques of the type illustrated in U.S. Pat. No. 3,855,208, incorporated herewith by reference, and Weetal, supra.

In a preferred embodiment, one uses the method where the ligand is an iodothyronine compound (see Tietz, Fundamentals of Clinical Chemistry, page 824, W. B. Saunders Company, Philadelphia, 1976), preferably L-thyroxine ($T_4$) or L-triiodothyronine ($T_3$), preferably where the ligand is labeled with a radioactive isotope, preferably iodine, and more preferably $^{125}I$. In another preferred embodiment one uses polyamide polymer test tubes in which the polymer comprises nylon, preferably nylon or polycaprolactam. The thermal activation, according to the invention, occurs during the injection molding of the test tubes by a procedure and cycle time that are generally conventional (as described, for example, in 1981-1982, Modern Plastics Encyclopedia, seriatim at pages 32, 315, 332, 336, 777 et seq., McGraw-Hill, New York), but is modified by carrying out the injection at a constant elevated mold temperature ranging from about 450° to 530° F. and for nylon 6 preferably at about 480° F. whereby the surfaces of the resulting molded parts are activated and uniformly so activated, to provide reactive centres or binding sites for purposes of the invention. These sites at the molecular level, are believed to comprise functional groups such as free polyamide amino and carboxyl groups (see Weetal, supra, for a similar description involving hydrolysis).

For the present assay method, one uses a molded polyamide polymer test tube of given geometry (substantially like that depicted in U.S. Pat. No. 3,464,798, aforementioned) having a ligand-free mold-activated inner wall surface. One such tube structure and configuration that is preferred is a conventional shape of disposable plastic test tube (U.S. Pat. No. 3,855,208) measuring 12 (diameter)×75 mm. (Falcon Plastics, Los Angeles, Calif.). Thus, while the instant test tube can be conventional in structure and appearance, it differs from prior art tubes in that its surface, and particularly its inner surface that comes in contact with liquid contained in the test tube, is uniquely activated, being formed (by the plastic molding step itself) with binding sites that are specific for particular ligand or ligands of interest. While the entire inner surface of the tube (as opposed to a selected portion thereof) can be so activated for purposes of the invention, the area of exposure or surface area actually used for binding (namely, the lowermost portion) can be predetermined simply by selecting the correct volume of liquid sample used in the test tube that will contact the surface area in question when the tube is held in a fixed (e.g., vertical) position. In this way, the ligand binding capacity for assay purposes can be made uniform from tube to tube. The assay concept of the invention, aside from the use of the novel thermally activated container means, is generally conventional. Thus, in this respect, one may use broadly all of the available assay technology that is known in the art or otherwise available for the determination of ligand content of samples employing labeled and unlabeled ligand and ligand binding protein and involving incubation or other procedure to provide bound and unbound solid and liquid phases, separation thereof and counting or determining the ligand content of the sample.

In another aspect, the invention concerns means, preferably in the form of a test pack or test kit, for the determination of ligand content in aqueous samples, comprising a plurality of molded polyamide polymer test tubes each having a ligand-free inner wall surface of given area formed with thermally activated ligand-specific binding sites such that the ligand binding capacity for assay purposes is uniform from tube to tube, a first reagent comprising labeled ligand, and a second reagent comprising ligand binding protein. The first reagent, using the method described above, is intended to be contacted in respective ones of the test tubes with a sample containing the ligand and with the second reagent to bind part of the labeled and unlabeled ligand to the wall surface of each such test tube to produce a two-phase system wherein the solid phase includes the bound part of the labeled and unlabeled ligand and the liquid phase includes the unbound labeled and unlabeled ligand, and the label value of each phase when separated being a function of the ligand concentration that is referable to standards and controls. A preferred test pack for these purposes is one where the ligand is an iodothyronine such as $T_3$ or $T_4$.

In another aspect, as indicated above, the invention concerns a molded polymer container or test tube adapted to contain an aqueous biological or clinical sample for assay purposes, made (as described above) by molding polymeric polyamide plastic feed stock at controlled molding temperature. The molding conditions (using conventional injection molding equipment) are such that the wall surface of the resulting molded tube is formed with thermally activated binding sites serving, during assay, for binding attachment to any measurable quantity of attachable ligand or ligand conjugate present in the aqueous content of the thus activated, molded container tube. The invention contemplates that the container tubes unlike prior art container substrates, can be used as stock items with an indefinite shelf life that do not require refrigeration or other special handling. The tubes are applicable for the assay of a wide variety of ligands, particularly for the assay of thyroid hormones in blood serum and more particularly an iodothyronine such as $T_3$ and $T_4$. A preferred polyamide plastic feed stock material for making the container tubes is nylon, especially nylon 6. Also preferred is polyamide plastic feed stock material that is injection molded by otherwise conventional means and cycle times but at constant mold temperature ranging from about 450° to about 530° F. and for nylon 6 preferably about 480° F. such that thermally activated binding sites are thereby produced and also are produced uniformly from tube to tube and uniformly on the surfaces of each of the resulting molded tubes, especially the inner wall surfaces of each tube. Thus, the binding capacity per unit of surface area for each tube produced is constant. The mold temperature employed may vary depending on the kind of polyamide plastic feed material employed for injection molding. The optimal temperature for each type or grade of feed material can be determined by routine experimentation. Thus, for a given polyamide resin feed material, one can ascertain the mold temperature that will give the best activation and the most active sites by a systematic trial procedure in which for a series of molding runs the mold temperature is varied at 10-degree increments within the prescribed mold temperature range. A preferred feed material is nylon 6, more preferably Type 6, 42L-N supplied by Wellman, Inc. Plastics Div., Boston.

The invention and the best mode of carrying out the same are illustrated by the following examples in which container tubes of the invention are used for the assay of serum iodothyronine ligand using $^{125}$I radioactively labeled ligand tracer, this procedure being typical for the assay of any of a wide variety of ligands.

EXAMPLE 1

DETERMINATION OF THYROXINE ($T_4$)

Materials and Reagents

A. Resin Tubes. 50 (12×75 mm.) mold-activated polyamide polymer test tubes made by injection molding of nylon 6 (Wellamid ®, Type 6, 42L-N, Wellman, Inc., Plastics Div., Boston) feed stock at a molding temperature of 480° F.

B. $^{125}$I Thyroxine ($T_4$) Tracer Solution. Contains 0.002 M 8-anilino-1-naphthylenesulfonic acid, 0.05 M phosphate buffer (pH 7.5), and 0.1% sodium azide.

C. Thyroxine ($T_4$) Antiserum Solution. Contains 0.05 M phosphate buffer (pH 7.5) and 0.1% sodium azide.

D. Lyophilized Reference Serum.

Specimen Collection

Sample. A minimum of 0.2 cc. of serum is required for the analysis. Samples should be collected directly into a vacuum collection tube.

Storage. Patient samples may be stored up to one week after collection at 2°–8° C.

Required Equipment

1. Gamma counter (for $^{125}$I).
2. Centrifuge (2500–5000 RPM).
3. Micropipettors (25 and 400 microliters) with disposable tips.

Procedure

1. Add 25 microliters of standardized reference serum or patient serum samples to the appropriate labeled tubes.
2. Dispense 0.5 ml. of thyroxine ($T_4$) tracer to each tube.
3. Shake all tubes to mix.
4. Dispense 0.5 ml. of thyroxine ($T_4$) antiserum to each tube, except the total count tubes.
5. Incubate at 37° C. for one hour.
6. Decant all tubes except total count tubes.
7. Count all tubes in the gamma counter for one minute.
8. Determine concentration (micrograms/deciliter) of thyroxine ($T_4$) by reference to $T_4$ reference standard and controls.

A typical determination for $T_4$ concentration in serums of three patients is tabulated as follows.

| DETERMINATION OF $T_4$ CONTENT - PATIENT SERA NOS. 1–3 | | | | |
|---|---|---|---|---|
| Reference Standard (micrograms per deciliter) | Solid Phase Radioactivity B (Ave. CPM) | B B50 | B | $T_4$ Value (Micrograms per deciliter) |
| 0 | 14547.5 | 22.7% | 10.5% | |
| 2.7 | 21118.5 | 33% | 15.8% | |
| 6 | 27708.5 | 43.2% | 20% | |
| 12.5 | 39664.5 | 62% | 28.5% | |
| 25 | 52531 | 82% | 37.7% | |
| 50 | 64067 | 100% | 46% | |
| TOTAL (bound and unbound) | 139091 | | | |
| Patient #1 | 18459 | 28.8% | | 1.3 |
| Patient #2 | 31685 | 49.45% | | 7.5 |
| Patient #3 | 44078 | 68.8% | | 16.8 |

The foregoing procedure can also be carried out using a different ligand instead of thyroxine, such as a coupled ligand in which thyroxine is coupled with a polycyclic entity such as 3-succinyl digoxigenin-L-thyroxine or 3-succinyl digoxigenin L-thyroxine peptide made by the methods described in U.S. Pat. No. 3,855,208.

EXAMPLE 2

$T_3$ UPTAKE ASSAY PROCEDURE

Materials and Reagents

A. Resin Tubes. 50 (12×75 mm.) mold-activated polyamide polymer test tubes made by injection molding of nylon 6 (42 L-N, Wellman) feed stock at a molding temperature of 480° F.

$^{125}$I $T_3$ Tracer Solution. Contains 0.05 M phosphate buffer (pH 7.5) and 0.1% sodium azide.

C. Lyophilized Reference Serum.

Specimen Collection

Sample. A minimum of 0.2 cc. of serum is required for the analysis. Samples should be collected directly into a vacuum collection tube.

Storage. Patient samples may be stored up to one week after collection at 2°–8° C.

Required Equipment

1. Gamma counter (for $^{125}$I).
2. Centrifuge (2500–5000 RPM).
3. Micropipettors (25 and 400 microliters) with disposable tips.

Procedure

1. Add 25 microliters of standardized reference serum or 25 microliters of patient serum samples to the appropriate labeled tubes.
2. Dispense 1.0 ml. of $T_3$ tracer to each tube.
3. Shake all tubes to mix.
4. Incubate at 37° C. for one-half hour.
5. Decant all tubes except total count tubes.
6. Count all tubes in the gamma counter for one minute.
7. Determine $T_3$ Uptake (percent) by reference to $T_3$ Standard.

A typical calculation for $T_3$ concentration is tabulated as follows.

| $T_3$ UPTAKE ASSAY DATA | | | |
|---|---|---|---|
| | CPM | Bound Bound/Control | $T_3$ Uptake (%) |
| Control Serum | 16235. | | 28.3 |

-continued

| T3 UPTAKE ASSAY DATA | | | |
|---|---|---|---|
| | CPM | Bound Bound/Control | T3 Uptake (%) |
| Patient #1 | 11629. | 71.6% | 20.3 |
| Patient #2 | 17480. | 107.7% | 30.5 |
| Patient #3 | 20972.5 | 129% | 36.6 |

While the invention is described in detail in the foregoing specification, it will be realized by those skilled in the art that considerable variation can be made in such detail without departing from the spirit and scope of the claims which follow.

I claim:

1. Means for the determination of ligand content in aqueous samples, comprising:
   a plurality of molded polyamide polymer test tubes made by molding polymeric polyamide plastic feed stock at controlled mold temperature for stability such that each has a ligand-free inner wall surface of given area formed with thermally activated ligand-specific binding sides whereby the ligand binding capacity for assay purposes is uniform from tube to tube,
   a first reagent comprising labeled ligand,
   a second reagent comprising ligand binding protein,
   the first reagent being intended to be contacted in respective ones of the test tubes with a sample containing the ligand and with the second reagent to bind part of the labeled and unlabeled ligand to the wall surface of each such test tube to produce a two-phase system, the two-phase system comprising a solid phase and a liquid phase wherein the solid phase includes the bound part of the labeled and unlabeled ligand and the liquid phase includes the unbound labeled and unlabeled ligand, and the label value of each phase when separated being a function of the ligand concentration that is referable to standards and controls.

2. Means according to claim 1 where the ligand is an iodothyronine compound.

3. Means according to claim 2 where the ligand is thyroxine.

4. Means according to claim 2 where the ligand is triiodothyronine.

5. A molded polymer container or test tube for an aqueous biological or clinical sample for assay purposes, made by molding polymeric polyamide plastic feed stock at controlled mold temperature such that the wall surface of the resulting molded tube is formed with thermally activated binding sites serving, during assay, for binding attachment to any measurable quantity of attachable ligand or ligand conjugate present in the aqueous content of the thus activated, molded container tube.

6. A container tube according to claim 5 where the polyamide plastic is nylon 6.

7. A container tube according to claim 5 where the mold temperature is in the range from about 450° to about 530° F.

8. A container tube according to claim 5 where the mold temperature is about 480° F.

9. A container tube according to claim 5 having binding sites for attachment to an iodothyronine ligand.

10. A container tube according to claim 5 having binding sites for attachment to thyroxine.

11. A container tube according to claim 5 having binding sites for attachment to triiodothyronine.

12. An assay method for the determination of ligand content in aqueous samples which comprises:
    providing a plurality of molded polyamide polymer test tubes made by molding polymeric plastic feed stock at controlled mold temperatures for stability such that the resulting tubes each have a ligand-free inner wall surface of given area formed with thermally activated ligand-specific binding sites whereby the ligand binding capacity for assay purposes is uniform from tube to tube,
    providing a tube set comprising said tubes each containing an aqueous sample of unlabeled ligand in admixture with labeled ligand binding protein, and further ones of said tubes containing comparable standards and controls
    incubating the mixtures contained in the tubes to achieve an end point wherein labeled and unlabeled ligand is bound to the respective tubes as a solid phase while unbound labeled and unlabeled ligand remains in the respective tubes as a liquid phase,
    separating the respective solid and liquid phases for each sample, and
    measuring the ligand content with respect to each sample as a function of the label value of at least one of the phases for that sample in relation to the standards and controls.

13. The method of claim 12 where the ligand is labeled with a radioactive isotope of iodine.

14. The method of claim 13 where the radioactive isotope is $^{125}$I.

15. The method of claim 12 where the polyamide polymer comprises nylon 6.

16. The method of claim 15 where the test tubes are produced by injection molding at a mold temperature in the range from about 450° to about 530° F.

17. The method of claim 15 where the test tubes are produced by injection molding at a mold temperature of about 480° F.

18. The method of claim 12 where the ligand is an iodothyronine compound.

19. The method of claim 12 where the ligand is thyroxine.

20. The method of claim 12 where the ligand is triiodothyronine.

* * * * *